(12) United States Patent
Cho et al.

(10) Patent No.: US 7,897,739 B2
(45) Date of Patent: Mar. 1, 2011

(54) METHOD FOR DIAGNOSING DIABETIC RETINOPATHY BY SINGLE NUCLEOTIDE POLYMORPHISM, DNA FRAGMENT THEREOF, AND PRIMER THEREOF

(75) Inventors: Yang-Je Cho, Seoul (KR); Bo-Young Ahn, Seoul (KR); Oh-Woong Kwon, Gyeonggi-do (KR); Suk-Joon Kim, Seoul (KR); Sun-Pyo Hong, Seoul (KR); Wang-Don Yoo, Seoul (KR); Soo-Ok Kim, Seoul (KR)

(73) Assignee: Eye-Gene, Inc., Seodae-Moon-Gu (KR)

( * ) Notice: Subject to any disclaimer, the term of this patent is extended or adjusted under 35 U.S.C. 154(b) by 224 days.

(21) Appl. No.: 11/920,402

(22) PCT Filed: May 18, 2005

(86) PCT No.: PCT/KR2005/001464

§ 371 (c)(1),
(2), (4) Date: Nov. 14, 2007

(87) PCT Pub. No.: WO2006/135117

PCT Pub. Date: Dec. 21, 2006

(65) Prior Publication Data

US 2009/0286233 A1    Nov. 19, 2009

(51) Int. Cl.
*C07H 21/02* (2006.01)
(52) U.S. Cl. .................................... 536/23.1
(58) Field of Classification Search ................ None
See application file for complete search history.

(56) References Cited

U.S. PATENT DOCUMENTS 5,474,796 A * 12/1995 Brennan .................... 427/2.13
2001/0053519 A1 * 12/2001 Fodor et al. .................... 435/6

OTHER PUBLICATIONS

Genbank Accession No. Y08736 (Oct. 27, 1997).*
Genbank Accession No. AR364544 (Sep. 3, 2003).*
Abe et al. (Tohoku J Exp Med. Nov. 2002;198(3):181-90).*
Buck et al ("Design Strategies and Performance of Custom DNA Sequencing Primers" Biotechniques. 1999. 27(3): pp. 528-536).*
Claffey et al. (Mol. Biol. Cell 1998 9: 469-481).*
Claffey, Kevin P., Shih, Shu-Ching, Mullen, Andrew, Dziennis Suzan, Cusick, Jennifer L., Abrams, Kristin R., Lee, Sam W., and Detmar, Michael; "Identification of a Human VPF/VEGF 3' Untranslated Region Mediating Hypoxia-induced mRNA Stability"; Molecular Biology of the Cell; vol. 9, No. 2, Feb. 1998; pp. 469-481.
Qaum, Tamin, Xu, Qingwen, Joussen, Antonia M., Clemens, Mark W., Qin, Wenying, Miyamoto, Kazuaki, Hassessian, Haroutioun, Wiegand, Stanley J., Rudge, John, Yancopoulos, George D., and Adamis, Anthony P.; "VEGF-initiated Blood-Retinal Barrier Breakdown in Early Diabetes"; Investigative Ophthalmology & Visual Science; vol. 42, No. 10, Sep. 2001; pp. 2408-2413.
Koga, Kaori, Osuga, Yutaka, Yoshino, Osamu, Hirota, Yasushi, Ruimeng, Xie, Hirata, Tetsuya, Takeda, Satoru, Yano, Tetsu, Tsutsumi, Osamu, Taketani, Yuji; "Elevated serum soluble vascular endothelial growth factor receptor 1 (sVEGFR-1) levels in women with preeclampsia"; The Journal of Clinical Endocrinology & Metabolism; vol. 88, No. 5, May 2003; pp. 2348-2351.
International Search Report for International Application No. PCT/KR2005/001464; mailed Feb. 15, 2006, p. 1.
Awata et al., *Brief Genetics Report* "A Common Polymorphism in the 5'-Untranslated Region of the VEGF Gene Is Associated With Diabetic Retinopathy in Type 2 Diabets", *Diabetes*, vol. 51, May 2002.
Ray et al., *Brief Genetics Report* "Association of the VEGF Gene With Proliferative Diabetic Retinopathy But Not Proteinuria in Diabetes", *Diabetes*, vol. 53, Mar. 2004 (pp. 861-864).
NCBI Assay ID: ss4251017, (reISNP ID: rs3025039), Entry date: Nov. 6, 2001 (7 pgs.).
NCBI Assay ID: ss4251018, (reISNP ID: rs3025040), Entry date: Nov. 6, 2001 (7pgs.).
NCBI Assay ID: ss4999276, (reISNP ID: rs3812867), Aug. 12, 2002 (1 pg.).
PCT International Search Report, based on International Application No. PCT/KR2005/001464, date of mailing of the International Search Report, Feb. 15, 2006 (1 pg.).

* cited by examiner

*Primary Examiner*—Christopher M. Babic
(74) *Attorney, Agent, or Firm*—Edwards Angell Palmer & Dodge LLP; Kongsik Kim (57) ABSTRACT

Disclosed is a method for diagnosing diabetic retinopathy by a single nucleotide polymorphism of VEGF and its receptor.

4 Claims, 10 Drawing Sheets

Flanking sequences of DMR-related SNPs
1. VEGF-rs3025039, Y=C/T

TGACAAGCCGAGGCGGTGAGCCGGGCAGGAGGAAGGAGCCTCCCTCAGGGTTT
CGGGAACCAGATCTCTCACCAGGAAAGACTGATACAGAACGATCGATACAGAAA
CCACGCTGCCGCCACCACACCATCACCATCGACAGAACAGTCCTTAATCCAGAA
ACCTGAAATGAAGGAAGAGGAGACTCTGCGCAGAGCACTTTGGGTCCGGAGGGC
GAGACTCCGGCGGAAGCATTCCCGGGCGGGTGACCCAGCAYGGTCCCTCTTGG
AATTGGATTCGCCATTTTATTTTTCTTGCTGCTAAATCACCGAGCCCGGAAGATT
AGAGAGTTTTATTTCTGGGATTCCTGTAGACACACCCACCCACATACATACATTT
ATATATATATATATATTATATATATATAAAAATAAATATCTCTATTTTATATATATAAA
ATATATATATTCTTTTTTTAAATTAACAGTGCTAATGTTATTGGTGTCTTCACTGGATGTATTTGACTGCTGTGGA

2. VEGF-rs3025040, Y=C/T

AGTTGGGAGGGGAATGTTCCCACTCAGATCCTGACAGGGAAGAGGAGGAGATGA
GAGACTCTGGCATGATCTTTTTTTTGTCCCACTTGGTGGGGCCAGGGTCCTCTC
CCCTGCCCAGGAATGTGCAAGGCCAGGGCATGGGGGCAAATATGACCCAGTTTT
GGGAACACCGACAAACCCAGCCCTGGCGCTGAGCCTCTCTACCCCAGGTCAGAC
GGACAGAAAGACAGATCACAGGTACAGGGATGAGGACACYGGCTCTGACCAGGAG
TTTGGGGAGCTTCAGGACATTGCTGTGCTTTGGGGATTCCCTCCACATGCTGCAC
GCGCATCTCGCCCCCAGGGGCACTGCCTGGAAGATTCAGGAGCCTGGGCGGCCT
TCGCTTACTCTCACCTGCTTCTGAGTTGCCCAGGAGGCCACTGGCAGATGTCCCG
GCGAAGAGAAGAGACACATTGTTGGAAGAAGCAGCCCATGACAGCTCCCCTTCCTGGGACTCGCCCTCATCCTCTT

3. VEGFR-rs3812867, Y=A/G
TCTTTTCTCCCTTGCTTTTTGCTTTTTTTCCTTTTCCTCCTCACATGTCTTAGGC
CTGCTAGAGGACTCCCGAGATGTTGCTCAGGCCAGCCAGTGATCCCTGGGGCTA
ACGGGCTTGTTGCCCTGGGTTTTGGGCTGCAGGGCTGGCCCAGTGGGGTACYTG
ATGCATTGGGTGATCAGTGCAGCTCCTCAATCAAACTGGTCCTGCGTGCCCTGAG
GTGGCGGGGGTTGGAGCAGGGAAGTCATTGGGTTTAGGAAGGATTTCTCTAACACTGAGTAACATGAGGATTTAGCAGTAGT

US 7,897,739 B2

METHOD FOR DIAGNOSING DIABETIC RETINOPATHY BY SINGLE NUCLEOTIDE POLYMORPHISM, DNA FRAGMENT THEREOF, AND PRIMER THEREOF

TECHNICAL FIELD

The present invention relates to a method for diagnosing diabetic retinopathy, more specifically to a method capable of being used for preventing and treating the diabetic retinopathy by analyzing single nucleotide polymorphisms of the diabetics to predict possibility to induce the diabetic retinopathy; and SNP gene fragments and primers used in the method.

BACKGROUND ART

Generally, diabetes is one of complex metabolic diseases that cause lesions in microvessels, resulting in wide disorders in systemic tissues including eyes, especially the most important one of the systemic diseases affecting eyes (Lee, TaeHee, Choi, YoungGil. *Diabetic vascular complications*, Seoul: Korean Medical Book Publisher (1993)). Amongst them, the diabetic retinopathy belong to one of the most severe complications, and has become social problems since improved lifestyles and advanced medical standards make the life expectance and the morbid period of diabetics longer (Klein R. et al, *Arch Opthalmol.* 102:520-532 (1984)). The diabetic retinopathy is divided into two groups: a non-proliferative diabetic retinopathy in which retinal lesions caused by vascular disorders are defined within the retina, and a proliferative diabetic retinopathy in which neovascular tissues infiltrate from the retina into a vitreous cavity (Green, In: Spencer WH, ed. Ophthalmic Pathology: an atlas and textbook. 4th ed. Philadelphia: WB Saunder; 1124-1129 (1996)). The diabetic retinopathy is diagnosed by characteristic structural changes in the fundus. Loss of eyesight due to the diabetic retinopathy results from vitreous hemorrhages and macular degeneration together with traction retinal detachment of a macula lutea in the proliferative diabetic retinopathy, and they may be effectively treated using laser treatments along with surgeries (Diabetic Retinopathy Study Report Number 14: Int Opthalmol Clin. 27:239-253 (1987)). Such a treatment may be undergone at a suitable stage to minimize side effects of the diabetic retinopathy and prevent loss of eyesight. Accordingly, medical examinations of the diabetic retinopathy and careful diagnoses should be often conducted to determine whether or not surgeries are operated. However, only an examination by means of fundus photography has been currently conducted in ophthalmic hospitals as the diagnosis method, and therefore it is difficult to diagnose the diabetic retinopathy at an early stage, and prevention and surgical operation times may be frequently missed.

An ability to detect changes in a DNA sequence is necessarily required for determining molecular basis of hereditary diseases and specifying polymorphisms and so on of genetics. Detection and diagnosis of hereditary mutations at a DNA level have been carried out using karyotyping, restriction fragment length polymorphisms (RFLPs) or variable nucleotide type polymorphisms (VNTRs), etc., and a single nucleotide polymorphism (SNP) method has recently been widely used.

It has been found that a certain SNP difference between VEGF, which is directly relevant to inducing the diabetic retinopathy, and VEGF receptor genes (IOVS 2001 42,10 pp 2408-13) is related to the diabetic retinopathy, and the said methods are used for diagnosing a high risk group to contribute to its prevention and treatment.

DISCLOSURE OF INVENTION

Technical Problem

Accordingly, the present invention is designed to solve the problems of the prior art, and therefore it is an object of the present invention to provide a method for preventing and treating diseases by predicting possibility to metastasize into retinal complications in diabetics using a simple diagnosis of genes.

Technical Solution

In order to accomplish the above object, the present invention provides a DNA fragment for diagnosing diabetic retinopathy, selected from the group consisting of a) a DNA fragment having a $2029^{th}$ T base of a vascular endothelial growth factor (VEGF) gene; b) a DNA fragment having a $1514^{th}$ T base of a VEGF gene; and c) a DNA fragment having a $4612^{th}$ G base of a VEGF receptor gene.

In the present invention, the DNA fragment of a) is preferably a DNA fragment set forth in SEQ ID NO: 1, the DNA fragment of b) is preferably a DNA fragment set forth in SEQ ID NO: 6, and the DNA fragment of c) is preferably a DNA fragment set forth in SEQ ID NO: 11.

The present invention also provides a forward primer for diagnosing diabetic retinopathy, selected from the group consisting of a primer of SEQ ID NO: 2 binding to the DNA fragment of a); a primer of SEQ ID NO: 7 binding to the DNA fragment of b); and a primer of SEQ ID NO: 12 binding to the DNA fragment of c).

The present invention also provides a reverse primer for diagnosing diabetic retinopathy, selected from the group consisting of a primer of SEQ ID NO: 3 binding to the DNA fragment of a); a primer of SEQ ID NO: 8 binding to the DNA fragment of b); and a primer of SEQ ID NO: 13 binding to the DNA fragment of c).

Also, the present invention also provides a method for or diagnosing diabetic retinopathy using DNA sequencing, PCR-SSCP (Polymerase chain reaction-Single stranded conformation polymorphism), allele-specific hybridization, oligo-ligation method, mini-sequencing, enzymatic cleavage or DNA chip by using the DNA fragments according to the present invention as a template.

In the present invention, the enzymatic cleavage includes steps: a) amplifying the certain polynucleotide DNA fragment, including a certain SNP sequence as described herein, using the forward primers and the reverse primers; b) cleaving the amplified certain polynucleotide DNA fragment using restriction enzymes; and c) measuring molecular weights of the cleaved fragments.

The restriction enzymes, which may be used herein, are preferably selected from the group consisting of MmeI, ZraI, AlwI, BsgI, FokI and BstF5I, and FokI or BstF5I is most preferred.

BRIEF DESCRIPTION OF THE DRAWINGS

These and other features, aspects, and advantages of preferred embodiments of the present invention will be more fully described in the following detailed description, taken accompanying drawings. In the drawings.

BEST MODE FOR CARRYING OUT THE INVENTION

Hereinafter, preferred embodiments of the present invention will be described in detail referring to the accompanying drawings.

The present invention provides a method for pre-diagnosing or diagnosing possibility to metastasize into retinal complications in the diabetics by examining changes of the 1514th base (Mol. Biol. Cell 9 (2), 469-481 (1998)) and the 2029th base of a VEGF (Vascular endothelial growth factor) gene, and the 4612th base of a VEGF-R (receptor) gene (J. Clin. Endocrinol. Metab. 88(5), 2348-2351, (2003)) from living organisms.

The present invention provides diagnostic agents for examining changes of the 1514th base and the 2029th base of a VEGF gene, and the 4612th base of a VEGF-R gene from living organisms. Various methods may be used for examining changes of the 1514th base and the 2029th base of a VEGF gene, and the 4612th base of a VEGF-R gene.

For example, methods such as DNA sequencing, PCR-SSCP (Polymerase chain reaction-Single stranded conformation polymorphism), allele-specific hybridization, an oligo-ligation method, mini-sequencing, enzymatic cleavage and chips (for example, DNA chips) may be used in the present invention.

A Maxam-Gilbert method and A Sanger method have been used for the DNA sequencing, but the Sanger method has been currently widely used. The PCR-SSCP (Orita, M. et. al, Genomics, 1989, 5:8874-8879) is carried out by amplifying a sequence including a target SNT using a PCR system, dividing the resultant PCR product into each lane, followed by carrying out an electrophoresis in a polyacrylamide gel. The allele-specific hybridization is a method that examines whether or not DNA bases are changed by hybridizing probes, attached to a nylone filters and so on, with sample DNAs labeled with a radioactive isotope, and then adjusting a hybridizing condition such as temperature and so on. The oligo-ligation method (Nucleic Acid Research 24, 3728, 1996) is a method that carries out a ligation reaction, and then confirms presence of ligated products under a condition that a template DNA is ligated with a sequence that is not complementary to the template DNA. The mini-sequencing (Genome Research 7:606, 1997) is a method developed for an SNP scoring, wherein the method is designed to adjust a polymerization condition so that only one base to be substituted can be polymerized so as to confirm whether or not the base is mutated, and detect the one substituted base under different conditions depending on which base is substituted in the target site of the polymerized sequence.

The enzymatic cleavage (WO 01/90419) is a method that confirm presence of substituted bases by amplifying a target DNA sequence using a method such as PCR, digesting amplified products, containing a sequence that may be digested with or recognized by restriction enzymes, with two restriction enzymes to yield its fragments, and then measuring a molecular weight of the resultant fragments.

A principle of a method using the DNA chip is identical to the allele-specific hybridization, except that an oligonucleotide probe and so on is attached to a fixed phase.

MODE FOR THE INVENTION

Hereinafter, non-limiting examples will be described in detail with reference to the accompanying drawings.

Example 1

Substitution of 2029th Base of VEGF Gene

1. PCR amplification and Cleavage by restriction enzymes

A sequence of Template DNA (5'→3') is represented, as follows.

```
                                               (SEQ ID NO: 1)
AGAAAGACAGATCACAGGTACAGGGATGAGGACACcGGCTCTGACCAGGA

GTTTGGGGAGCTTCAGGACATTGCTGTGCTTTGG
```

The underlined sequence is regions binding to the following primers 1 and 2. The bases represented as a small letter are "modified bases".

```
Primer 1:
                                               (SEQ ID NO: 2)
5'-AGATCACAGGTACAGGGAggatgGAGGACAC-3' (31 mer)

Primer 2:
                                               (SEQ ID NO: 1)
5'-AGCAATGTCCTGAAGCTCCCCAAACTCCTG-3' (30 mer)
```

The sequence represented as a small letter is a recognition sequence of restriction enzymes FokI and BstF5I.

PCR buffer (1×), 2 mM MgSO$_4$, 200 µM dNTP, 0.315U of Platinum Taq Polymerase (Invitrogen, 10966-026), 0.5 µM primers 1 and 2, and 36 ng of genomic DNA were added and adjusted to the total volume of 18 µM. And, PCR reaction was performed, as follows.

94° C. 5 min,
94° C. 30 sec 55° C. 30 sec 72° C. 30 sec (35 cycles),
72° C. 5 min.

The genomic DNA was extracted from blood, and purely separated using conventional methods. For example, a 'SDS/ Protease K' method may be used herein. DNA may be extracted from blood using a method as described in Maniatis, Molecular Cloning, A laboratory Manual, Cold Spring Harber Laboratory Press, Cold Spring Harbor, 1989, or a QIAamp DNA Mini Kit 250 (Qiagen 51106). If the DNA is at a low concentration, then the DNA may be concentrated for use, as follow. To a DNA solution were 3 M sodium acetate (pH 5.3) of ⅒ volume of the solution and ethanol of 2.5 volume of the solution, gently mixed, and then kept at −20° C. for at least 1 hours. The resultant solution was centrifuged at 4° C. in 13,000 rpm for 15 minutes. Supernatant was carefully removed to obtain a pellet, and 70% ethanol was added to the pellet and centrifuged at 4° C. in 13,000 rpm for 10 minutes. Ethanol was completely removed to dryness, and then the pellet was dissolved in a suitable amount of distilled water.

Sequences of the fragments produced through the PCR are represented (5'→3'), as follows.

(SEQ ID NO: 4)
AGATCACAGGTACAGGGAggatgGAGGACAC[C/T]GGCTCTGACCAGGA

GTTTGGGGAGCTTCAGGACATTGCT (SEQ ID NO: 5)
TCTAGTGTCCATGTCCCTcctacCTCCTGTG[G/A]CCGAGACTGGTCCT

CAAACCCCTCGAAGTCCTGTAACGA

A region represented as a small letter is a sequence recognized by restriction enzymes FokI and BstF5I, underlined regions are sequences generated by cleavage of the restriction enzymes, and DNA bases represented in brackets ([ ]) are "modified bases". 1 U FokI (NEB R109L), 1 U BstF5I (NEB, V0031L), 5 mM potassium acetate, 2 mM Tris-acetate, 1 mM magnesium acetate, and 0.1 mM DTT (pH 7.9, at 25° C.) were added to the reaction, and the resultant mixture was reacted at 25° C. for 2 hours, followed by at 45° C. for 2 hours.

2. Purification and Desalination

Molecular weights of DNA fragments are preferably measured after the DNA fragments were purely separated from the above solution treated with the restriction enzymes. For example, NuCleave™ Genotyping Kit (Variagenics, USA) may be used herein. At first, 70□ of IM TEAA (Triethylammoniumacetate, pH 7.6) was added to the restriction-enzyme reaction solution and kept for 1 minute. 70□ of 1 M TEAA and 90□ of the said mixture solution were sequentially added to pass through a sample preparation plate, and then 85□ of 0.1 M TEAA was passed through the sample preparation plate five times. The sample preparation plate was centrifuged at 1000 rpm for 5 minutes. The sample preparation plate was put on a collection plate, and 60□ of 60% isopropanol was added to pass through the sample preparation plate. If an elution solution was harvested into the collection plate, the collection plate was dried at 115° C. for 75 minutes.

3. MALDI-TOF Mass Spectrometry

6□ of MALDI matrix (22.8□ of ammonium citrate, 148.5□ of hydroxypicolinic acid, 1.12□ of acetonitrile, 7.8□ of $_2$IO) was added into a collection plate, and then 4□ out of 6□ of the MALDI matrix was put on an anchor chip plate of a MALDI-TOF (Biflex IV, Bruker). The anchor chip plate of MALDI-TOF was dried at 37° C. for 30 minutes, kept at room temperature for a while to cool it, and then analyzed using a MALDI-TOF.

An analysis method is conducted according to a manual of the MALDI-TOF.

Figure 1:
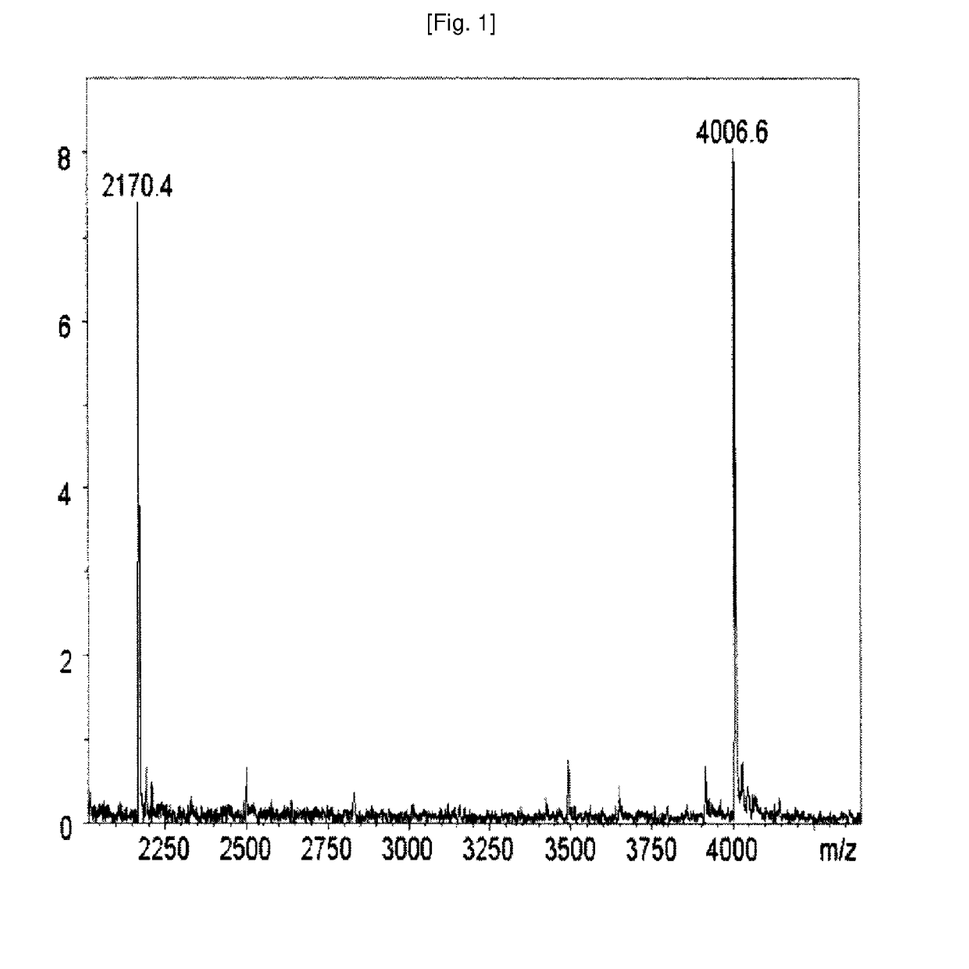
FIG. 1 is a diagram showing that molecular weights of the resultant fragments are 2170.4 daltons (7 mers) and 4006.6 daltons (13 mers) after cleavage of Chr6 by enzymes if the $43754466^{th}$ base of Chr6 is CC, using a MALDI-TOF.
Figure 2:
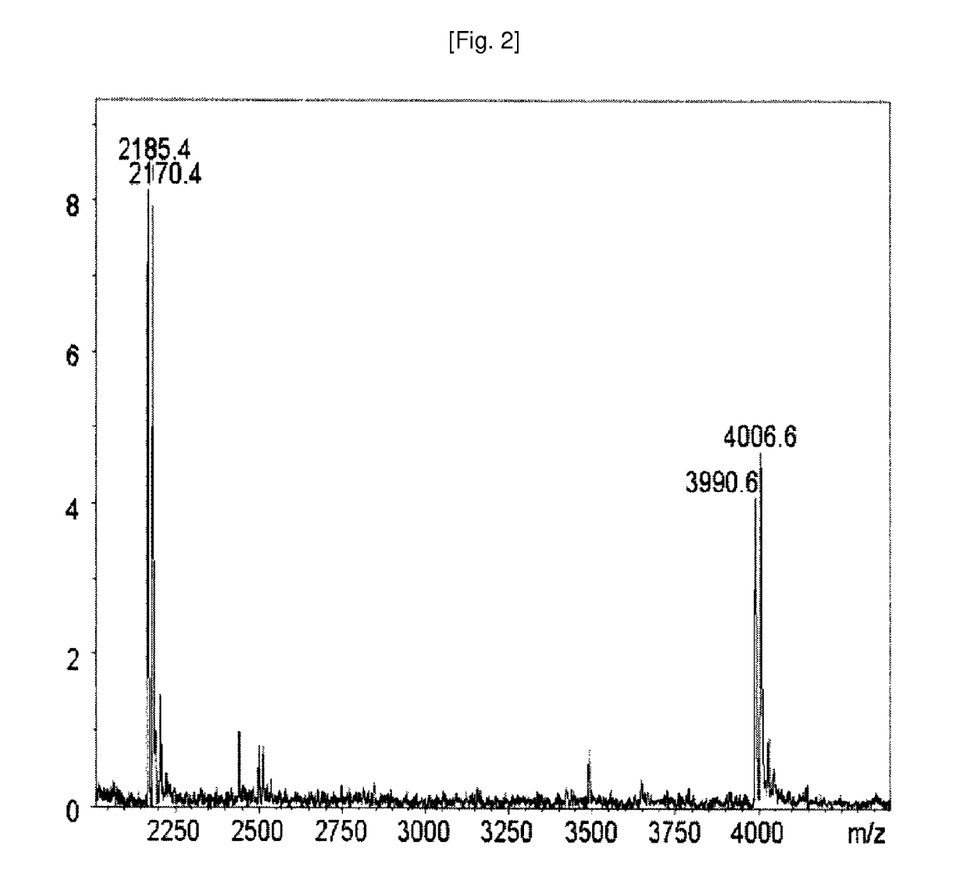
FIG. 2 is a diagram showing that molecular weights of the resultant fragments are 2170.4 daltons, 2185.4 daltons (at least 7 mers), 4006.6 daltons and 3990.6 daltons (at least 13 mers) after cleavage of Chr6 by enzymes if the 43754466th base of Chr6 is CT, using a MALDI-TOF.
Figure 3:
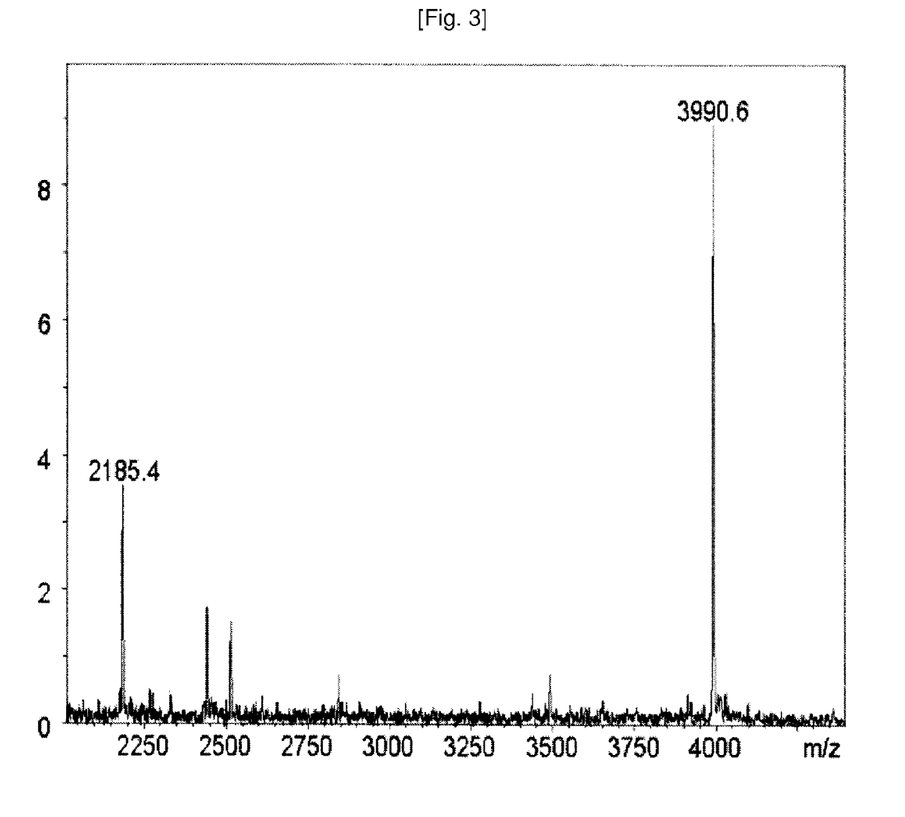
FIG. 3 is a diagram showing that molecular weights of the resultant fragments are 2185.4 daltons (7 mers) and 3990.6 daltons (13 mers) after cleavage of Chr6 by enzymes if the 43754466th base of Chr6 all is T (TT), using a MALDI-TOF.

If the 43754466$^{th}$ base of Chr6 is CC, molecular weights of the resultant fragments are 2170.4 daltons (7 mers) and 4006.6 daltons (13 mers) after cleavage of Chr6 by the enzymes (FIG. 1). If the 43754466$^{th}$ base of Chr6 is CT, molecular weights of the resultant fragments are 2170.4 daltons, 2185.4 daltons (at least 7 mers), 4006.6 daltons and 3990.6 daltons (at least 13 mers) after cleavage of Chr6 by the enzymes (FIG. 2). Meanwhile, if the 43754466$^{th}$ base of Chr6 all is T (TT), molecular weights of the resultant fragments are 2185.4 daltons (7 mers) and 3990.6 daltons (13 mers) after cleavage of Chr6 by the enzymes (FIG. 3).

Example 2

Substitution of 1514$^{th}$ Base of Human VEGF (Vascular Endothelial Growth Factor) Gene A template DNA sequence is represented, as follows.

(SEQ ID NO: 6)
GGCGGAAGCATTCCCGGGCGGGTGACCCAGCAcGGTCCCTCTTGGAATTG

GATTCGCCATTTTATTTTT

In the above sequence, underlined regions are sequences to which the following primers 3 and 4 bind, respectively. A DNA base represented as a small letter is "a modified base".

Primer 3:
(SEQ ID NO: 7)
5'-AAGCATTCCCGGGCGGGTggatgACCCAGCA-3'(31 mers)

Primer 4:
(SEQ ID NO: 8)
5'-TAAAATGGCGAATCCAATTCCAAGAGG-3'(27 mers)

In the above primers, a region represented as a small letter is a sequence that is not present in the template DNA, and therefore recognized by restriction enzymes FokI and BstF5I. An experimental method including a PCR reaction was repeated in the same manner as in Example 1.

Sequences of the fragments produced through the PCR are represented (5'→3'), as follows.

(SEQ ID NO: 9)
AAGCATTCCCGGGCGGGTggatgACCCAGCA[C/T]GGTCCCTCTTGGAA

TTGGATTCGCCATTTTA (SEQ ID NO: 10)
TTCGTAAGGGCCCGCCCAcctacTGGGTCGT[G/A]CCAGGGAGAACCTT

AACCTAAGCGGTAAAAT

In the above sequences, a region represented as a small letter is a sequence recognized by restriction enzymes, underlined regions are sequences generated by cleavage of the restriction enzymes, and DNA bases represented in brackets ([ ]) are "modified bases". 1 U FokI (NEB R109L), 1 U BstF5 I (NEB, V0031L), 5 mM potassium acetate, 2 mM Tris-acetate, 1 mM magnesium acetate, 0.1 mM DTT (pH 7.9, at 25° C.) were added to the reaction, and the resultant mixture was reacted at 25° C. for 2 hours, followed by at 45° C. for 2 hours.

Figure 4:
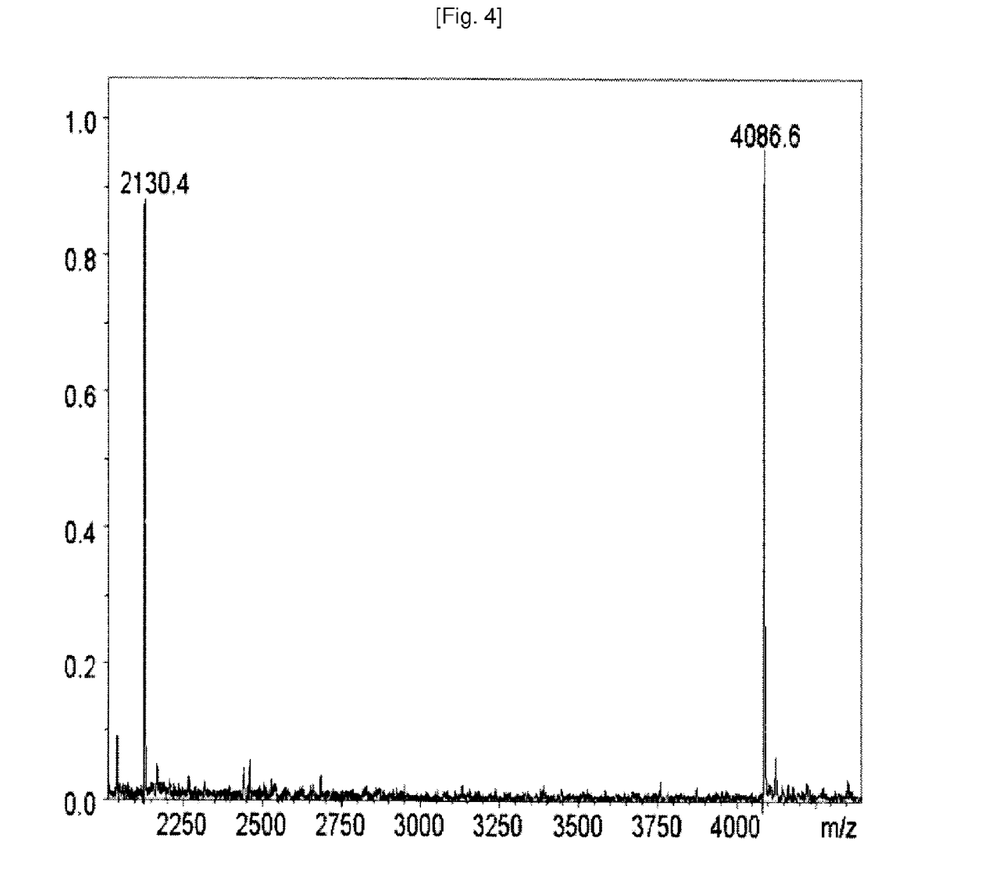
FIG. 4 is a diagram showing that molecular weights of the resultant fragments are 2130.4 daltons (7 mers) and 4086.6 daltons (13 mers) after cleavage of Chr6 by enzymes if the 43753951st base of Chr6 is CC, using a MALDI-TOF.
Figure 5:
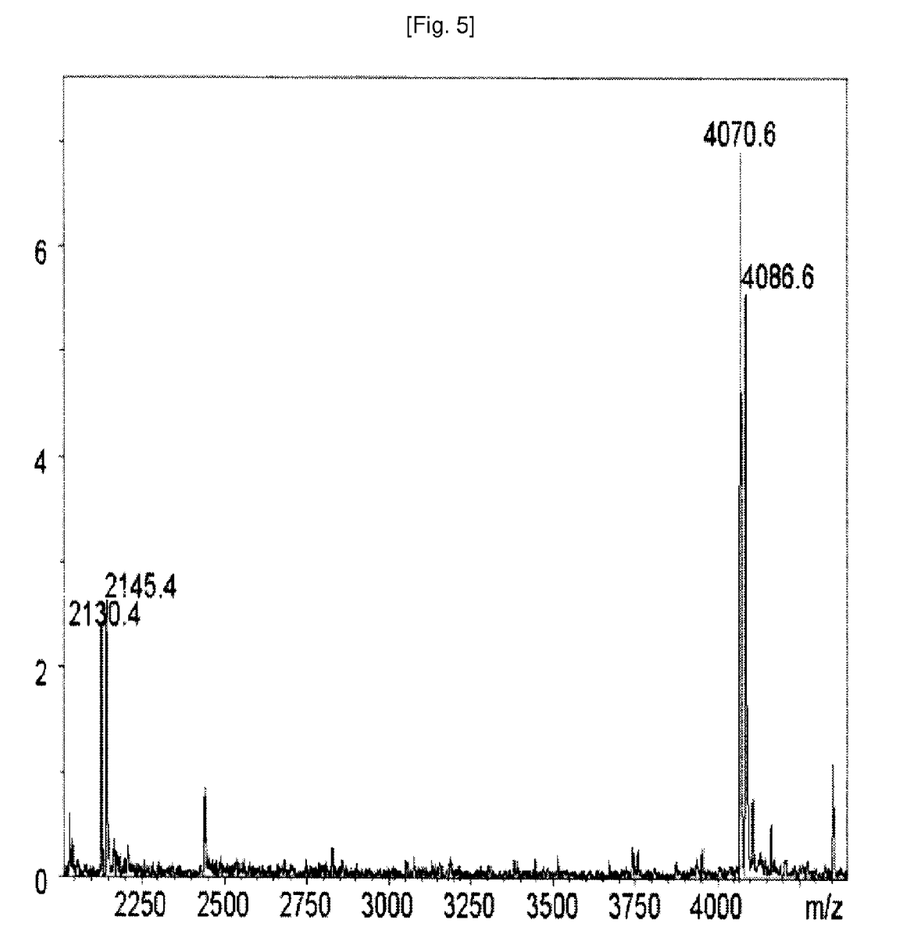
FIG. 5 is a diagram showing that molecular weights of the resultant fragments are 2130.4 daltons, 2145.4 daltons (at least 7 mers), 4086.6 daltons and 4070.6 daltons (at least 13 mers) after cleavage of Chr6 by enzymes if the 43753951st base of Chr6 is CT, using a MALDI-TOF.
Figure 6:
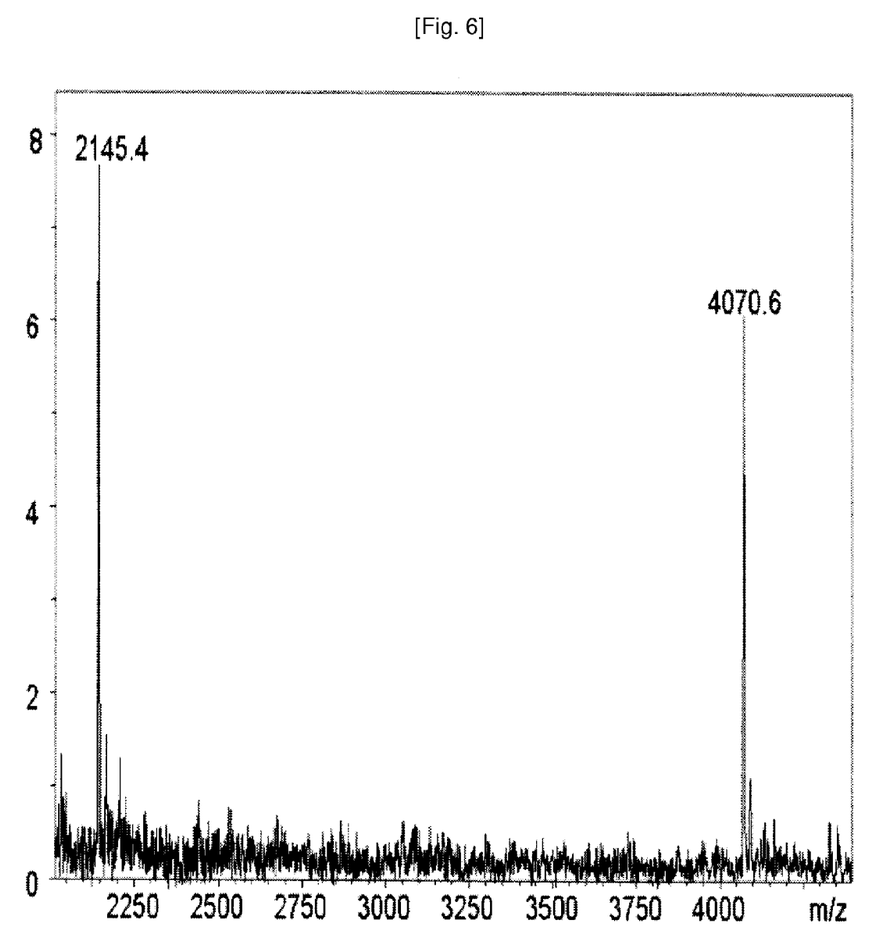
FIG. 6 is a diagram showing that molecular weights of the resultant fragments are 2145.4 daltons (7 mers) and 4070.6 daltons (13 mers) after cleavage of Chr6 by enzymes if the 43753951st base of Chr6 all is T (TT), using a MALDI-TOF.

If the 43753951st base of Chr6 is CC, molecular weights of the resultant fragments are 2130.4 daltons (7 mers) and 4086.6 daltons (13 mers) after cleavage of Chr6 by the enzymes (FIG. 4). If the 43753951st base of Chr6 is CT, molecular weights of the resultant fragments are 2130.4 daltons, 2145.4 daltons (at least 7 mers), 4086.6 daltons and 4070.6 daltons (at least 13 mers) after cleavage of Chr6 by the enzymes (FIG. 5). Meanwhile, if the 43753951st base of Chr6 all is T (TT), molecular weights of the resultant fragments are 2145.4 daltons (7 mers) and 4070.6 daltons (13 mers) after cleavage of Chr6 by the enzymes (FIG. 6).

Example 3

FMS-Related Tyrosine Kinase 1, rs3812867 (Chr13, 27806957)

A template DNA sequence is represented, as follows.

(SEQ ID NO: 11)
TTTTGGGCTGCAGGGCTGGCCCAGTGGGGTACaTGATGCATTGGGTGATC

AGTGCAGCTCCTCAATCAAACTGGTCCTG

In the above sequence, underlined regions are sequences to which the following primers 5 and 6 bind, respectively. A DNA base represented as a small letter is "a modified base".

Primer 5:
(SEQ ID NO: 12)
5'-GGCTGCAGGGCTGGCCCAggatgTGGGGTAC-3' (31 mers)

Primer 6:
(SEQ ID NO: 13)
5'-CCAGTTTGATTGAGGAGCTGCACTGATCAC-3' (30 mers)

In the above primers, a region represented as a small letter is a sequence that is not present in the template DNA, and therefore recognized by restriction enzymes FokI and BstF5I. An experimental method including a PCR reaction was repeated in the same manner as in Example 1.

Sequences of the fragments produced through the PCR are represented (5'→3'), as follows.

(SEQ ID NO: 14)
GGCTGCAGGGCTGGCCCAggatgTGGGGTAC[A/G]TGATGCATTGGGTG

ATCAGTGCAGCTCCTCAATCAAACTGG (SEQ ID NO: 15)
CCGACGTCCCGACCGGGTcctacACCCCATG[T/C]ACTACGTAACCCAC

TAGTCACGTCGAGGAGTTAGTTTGACC

In the above sequences, a region represented as a small letter is a sequence recognized by restriction enzymes, underlined regions are sequences generated by cleavage of the restriction enzymes, and DNA bases represented in brackets ([ ]) are "modified bases". 1 U FokI (NEB R109L), 1 U BstF5I (NEB, V0031L), 5 mM potassium acetate, 2 mM Tris-acetate, 1 mM magnesium acetate, and 0.1 mM DTT (pH 7.9, at 25° C.) were added to the reaction, and the resultant mixture was reacted at 25° C. for 2 hours, followed by at 45° C. for 2 hours.

Figure 7:
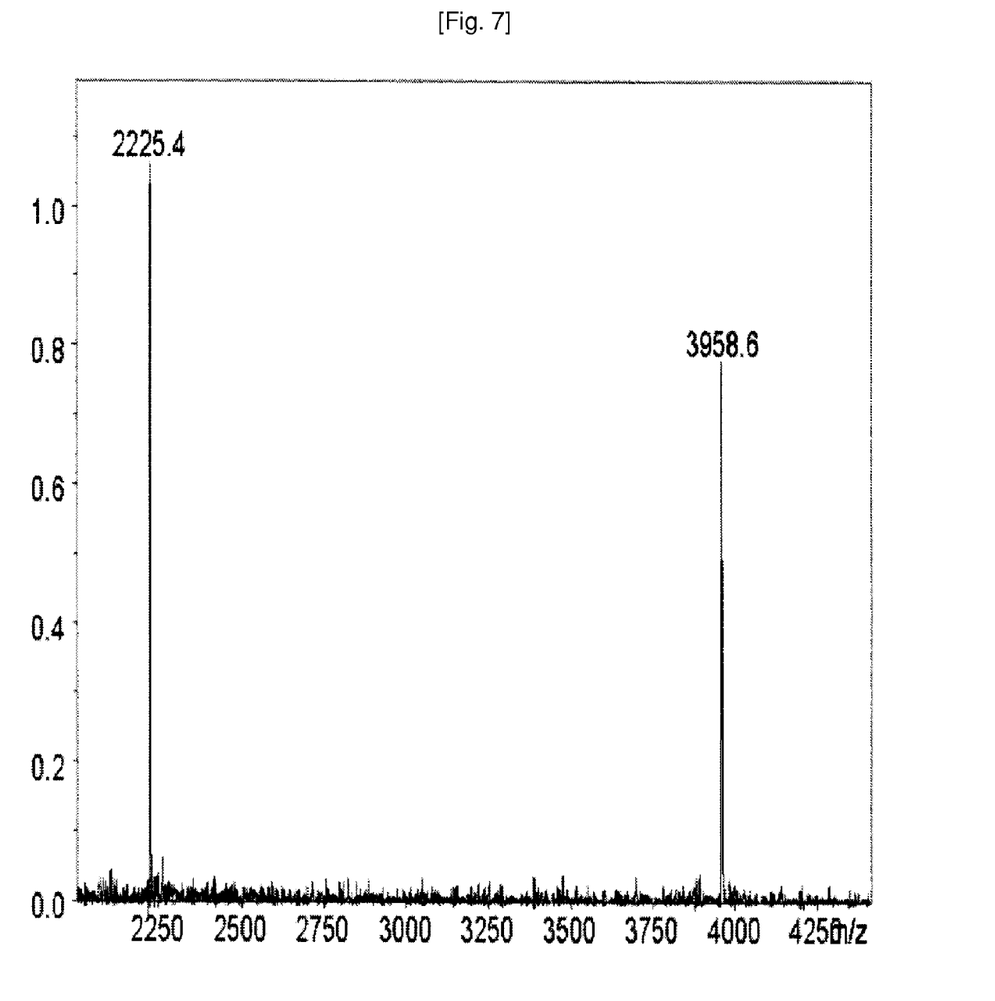
FIG. 7 is a diagram showing that molecular weights of the resultant fragments are 2225.4 daltons (7 mers) and 3958.6 daltons (13 mers) after cleavage of Chr13 by enzymes if the 27806957th base of Chr13 is AA, using a MALDI-TOF.
Figure 8:
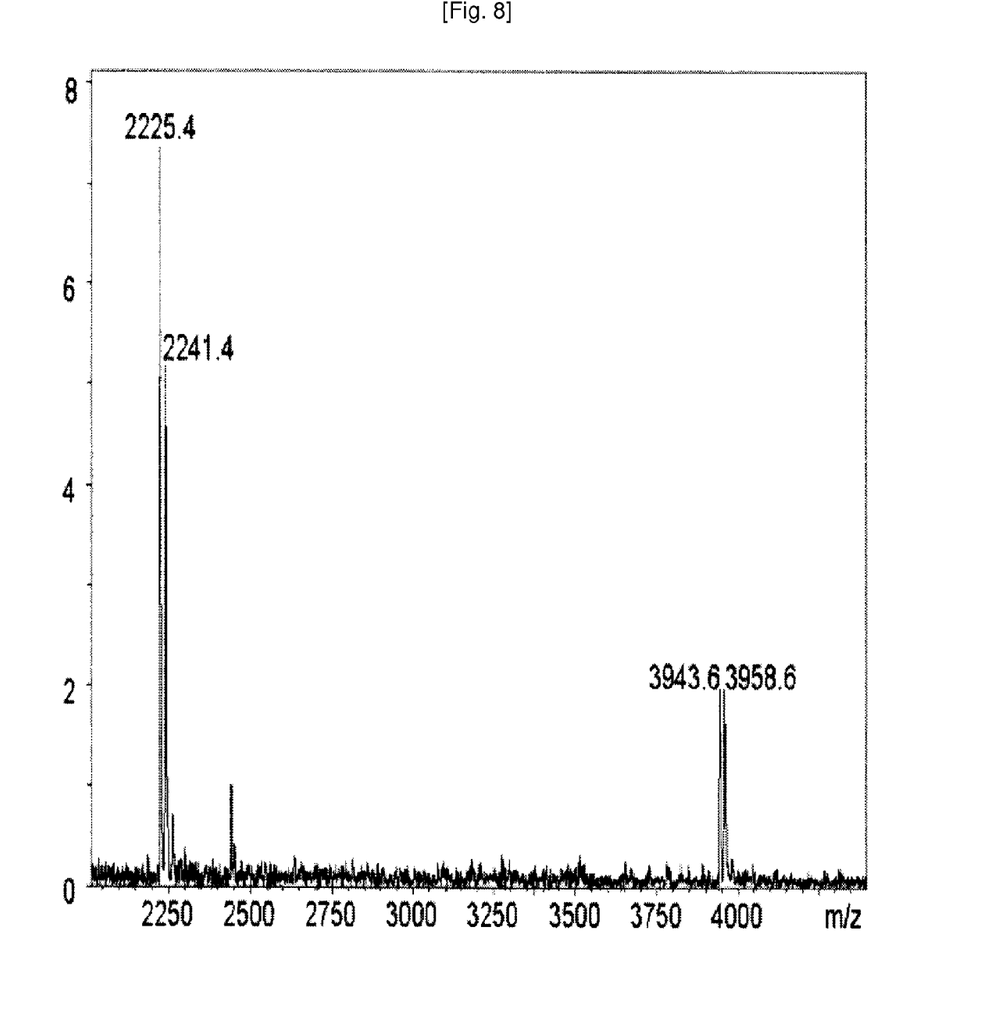
FIG. 8 is a diagram showing that molecular weights of the resultant fragments are 2225.4 daltons, 2241.4 daltons (at least 7 mers), 3958.6 daltons and 3943.6 daltons (at least 13 mers) after cleavage of Chr13 by enzymes if the 27806957th base of Chr13 is AG, using a MALDI-TOF.
Figure 9:
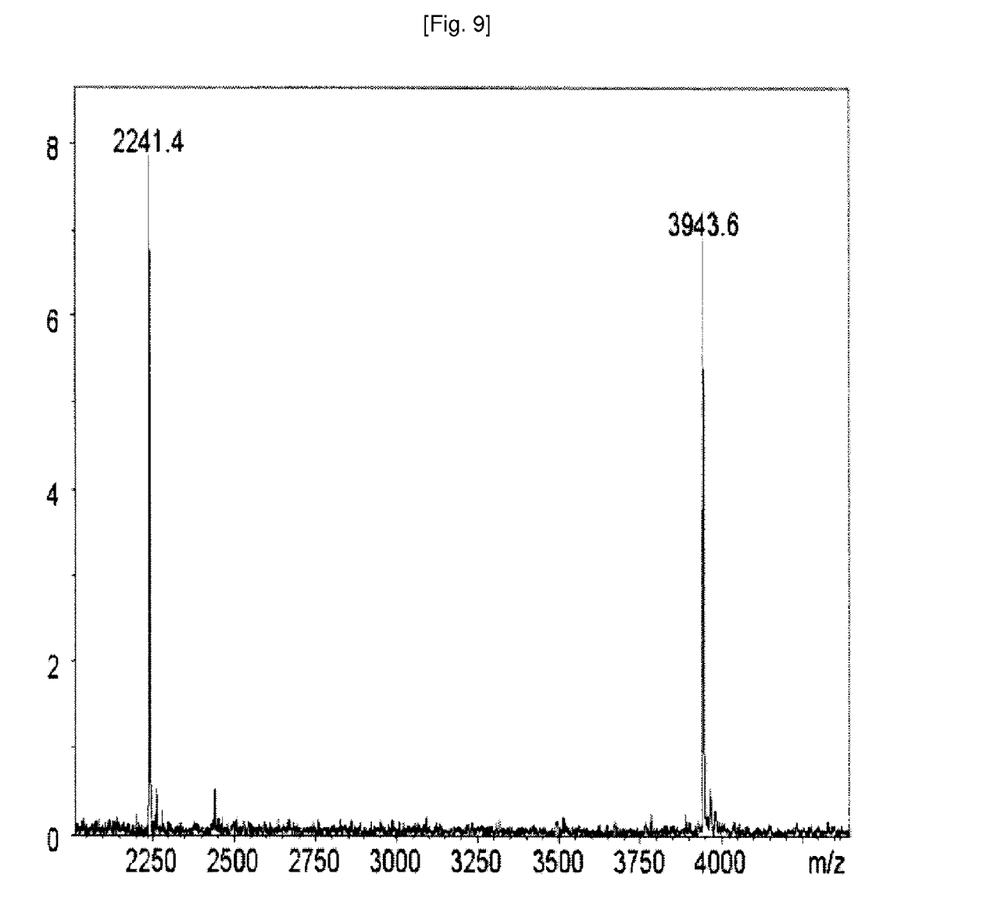
FIG. 9 is a diagram showing that molecular weights of the resultant fragments are 2241.4 daltons (7 mers) and 3943.6 daltons (13 mers) after cleavage of Chr13 by enzymes if the 27806957th base of Chr13 all is G (GG), using a MALDI-TOF.
Figure 10:
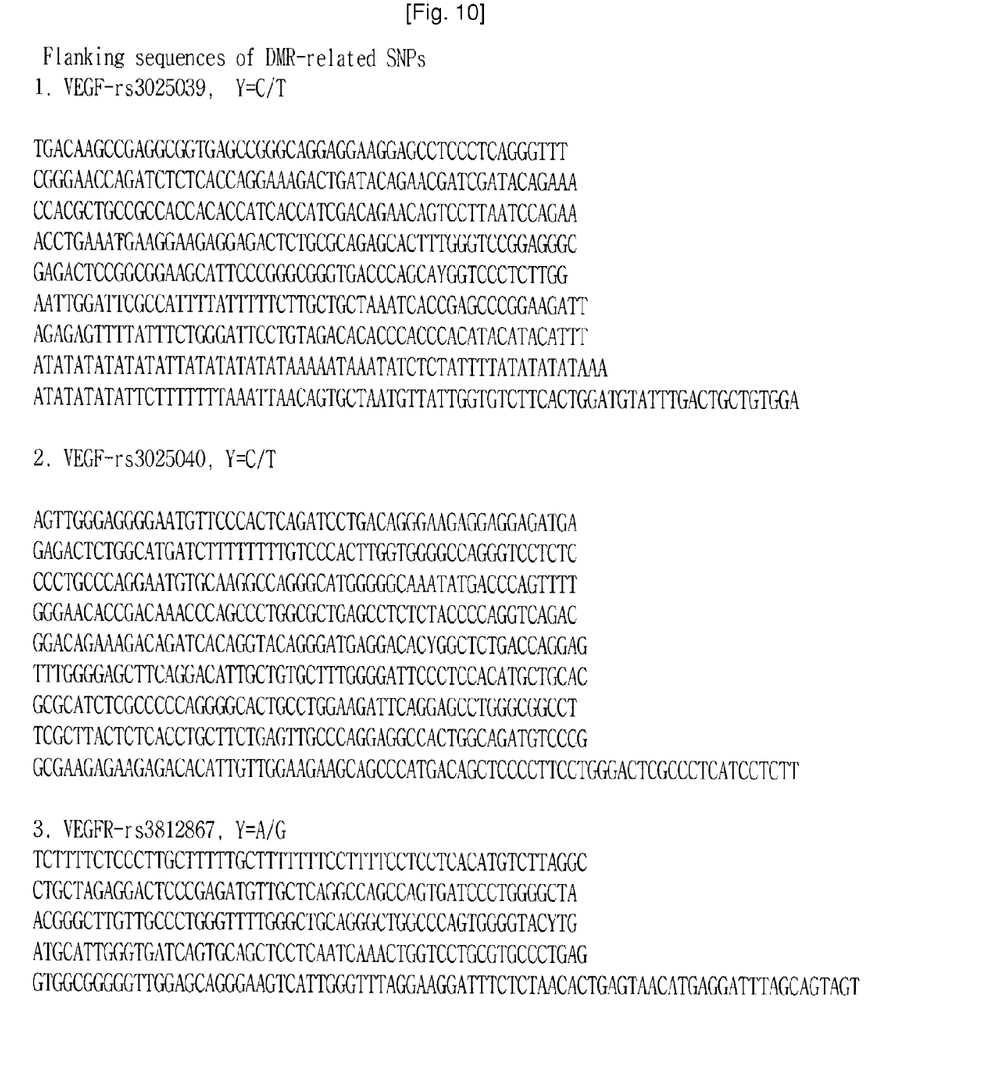
FIG. 10 is a diagram showing DNA sequences and locations of genes used for diagnosis: VEGF-rs3025039; VEGF-rs3025040, and VEGFR-rs3812867.1

If the 27806957th base of Chr13 is AA, molecular weights of the resultant fragments are 2225.4 daltons (7 mers) and 3958.6 daltons (13 mers) after cleavage of Chr13 by the enzymes (FIG. 7). If the 27806957th base of Chr13 is AG, molecular weights of the resultant fragments are 2225.4 daltons, 2241.4 daltons (at least 7 mers), 3958.6 daltons and 3943.6 daltons (at least 13 mers) after cleavage of Chr13 by the enzymes (FIG. 8). Meanwhile, if the 27806957th base of Chr13 all is G (GG), molecular weights of the resultant fragments are 2241.4 daltons (7 mers) and 3943.6 daltons (13 mers) after cleavage of Chr13 by the enzymes (FIG. 9).

Example 4

Frequency of Occurrence of Diabetics' Diabetic Retinopathy According to Base Substitution in rs3812867 (Chr13, 27806957). rs3025040 (Chr6, 43754466) and rs3025039 (Chr6, 43753951)

1. Sampling of Blood

Bloods were sampled from patients suffering from diabetes over 10 years, and an ophthalmologist goes through examinations of retinas to determine whether or not the patients have a diabetic retinopathy.

2. DNA Separation

DNA was separated from the sampled blood. DNA separation was conducted using a QIAamp DNA Blood Mini Kit from the company Qiagen.

3. SNP Analysis

Three parts of the SNP were analyzed according to Examples 1, 2 and 3. The results are listed in the following Table 1.

TABLE 1

| Association Study | | |
|---|---|---|
| 1) rs3025039 | | |
| | Diabetes (DM) | Diabetic retinopathy (DMR) |
| Rare allele | 7 | 25 |
| Common allele | 69 | 89 |
| Odds Ratio = 2.83 | Confidential interval: 1.06~12.31 | p = 0.0319 |
| 2) rs3025040 | | |
| Odds ratio is identical because of absolute linkage disequilibrium with rs3025039. | | |
| 3) rs3812867 | | |
| | Diabetes | Diabetic retinopathy |
| Rare allele | 2 | 12 |
| Common allele | 76 | 102 |
| Odds Ratio = 4.47 | Confidential interval: 2.01~15.20 | p = 0.0151 |

In Table 1, the number of the alleles represents the number of chromosomes having the allele bases. Since 38 patients have a DM and 57 patients have a DMR☐ 57, 76 patients have a DM chromosome and 114 patients have a DMR chromosome if 2 is multiplied by 38 and 57, respectively.

In a genotype-phenotype association study, the number of patients or alleles having a concerned genotype may be used as a variable x, and therefore the results are similar to each other. If rare homos are rich in patients, then the variable x is also set to 0, 1, 2 (CC, CT, TT, if rare allele=T) to calculate an additive effect, but the additive effect was analyzed using a 2×2 table since the homo of the rare allele is not rich in our patient group.

Odds ratios are generally used to compare the odds for two groups in a book of statistics, and often called "OR". The odds ratios are referred to as a risk associated with diseases if there is no factors.

In this patent, it indicates that if the rare allele is present in DM patients, a risk that the DM patients metastasize into DMR is higher 2.83 times (283%) and 4.47 times (447%) than that of DM patients otherwise having a common allele.

95% CI is referred to as a confidential interval on the assumption of normal distribution, a P value is referred to as an index showing statistic significance of OR (null hypothesis: the probability to obtain such a result flexibly), and the experimental result is proven to be statistically significant if the P value is generally lower than 0.05.

INDUSTRIAL APPLICABILITY

As listed in the table, it can be known that the increased number of rare alleles in a patient suffering from a diabetic retinopathy is statistically significant if he has a rare allele of snp in a specific location. Such a result suggests that persons having rs3025039 and rs3025040 rare allele groups of the VEGF gene and an rs3812867 rare allele group of the VEGFR gene has a higher risk to metastasize into a diabetic retinopathy than those who does not have the said rare allele groups.

The invention claimed is:

1. A DNA fragment for diagnosing diabetic retinopathy, wherein the DNA fragment is a DNA fragment of the VEGF receptor gene comprising the sequence set forth in SEQ ID NO:11.

2. The DNA fragment for diagnosing diabetic retinopathy according to claim 1, wherein the DNA fragment consists of the sequence set forth in SEQ ID NO:11.

3. A forward primer for use in a method of diagnosing diabetic retinopathy, said primer selected from the group consisting of:
   a primer having the sequence set forth in SEQ ID NO:2;
   a primer having the sequence set forth in SEQ ID NO:7; and
   a primer having the sequence set forth in SEQ ID NO:12.

4. A primer set for use in a method of diagnosing diabetic retinopathy, said primer set selected from the group consisting of:
   a forward primer having the sequence set forth in SEQ ID NO: 2 and a reverse primer having the sequence set forth in SEQ ID NO:3;
   a forward primer having the sequence set forth in SEQ ID NO: 7 and a reverse primer having the sequence set forth in SEQ ID NO:8; and
   a forward primer having the sequence set forth in SEQ ID NO: 12 and a reverse primer having the sequence set forth in SEQ ID NO:13.

* * * * *

SEQUENCE LISTING

<160> NUMBER OF SEQ ID NOS: 18

<210> SEQ ID NO 1
<211> LENGTH: 84
<212> TYPE: DNA
<213> ORGANISM: Artificial Sequence
<220> FEATURE:
<223> OTHER INFORMATION: VEGF DNA Fragment

<400> SEQUENCE: 1
agaaagacag atcacaggta cagggatgag gacaccggct ctgaccagga gtttggggag    60
cttcaggaca ttgctgtgct ttgg                                          84

<210> SEQ ID NO 2
<211> LENGTH: 31
<212> TYPE: DNA
<213> ORGANISM: Artificial Sequence
<220> FEATURE:
<223> OTHER INFORMATION: Primer 1 (forward primer)

<400> SEQUENCE: 2
agatcacagg tacagggagg atggaggaca c                                  31

<210> SEQ ID NO 3
<211> LENGTH: 30
<212> TYPE: DNA
<213> ORGANISM: Artificial Sequence
<220> FEATURE:
<223> OTHER INFORMATION: Primer 2 (reverse primer)

<400> SEQUENCE: 3
agcaatgtcc tgaagctccc caaactcctg                                    30

<210> SEQ ID NO 4
<211> LENGTH: 71
<212> TYPE: DNA
<213> ORGANISM: Artificial Sequence
<220> FEATURE:
<223> OTHER INFORMATION: Resulting DNA Fragment

<400> SEQUENCE: 4
agatcacagg tacagggagg atggaggaca cyggctctga ccaggagttt ggggagcttc    60
aggacattgc t                                                        71

<210> SEQ ID NO 5
<211> LENGTH: 71
<212> TYPE: DNA
<213> ORGANISM: Artificial Sequence
<220> FEATURE:

<223> OTHER INFORMATION: Resulting DNA Fragment

<400> SEQUENCE: 5

```
agcaatgtcc tgaagctccc caaactcctg gtcagagccr gtgtcctcca tcctccctgt    60
acctgtgatc t                                                         71
```

<210> SEQ ID NO 6
<211> LENGTH: 69
<212> TYPE: DNA
<213> ORGANISM: Artificial Sequence
<220> FEATURE:
<223> OTHER INFORMATION: VEGF DNA Fragment

<400> SEQUENCE: 6

```
ggcggaagca ttcccgggcg ggtgacccag cacggtccct cttggaattg gattcgccat    60
tttattttt                                                            69
```

<210> SEQ ID NO 7
<211> LENGTH: 31
<212> TYPE: DNA
<213> ORGANISM: Artificial Sequence
<220> FEATURE:
<223> OTHER INFORMATION: Primer 3 (forward primer)

<400> SEQUENCE: 7

```
aagcattccc gggcgggtgg atgacccagc a                                   31
```

<210> SEQ ID NO 8
<211> LENGTH: 27
<212> TYPE: DNA
<213> ORGANISM: Artificial Sequence
<220> FEATURE:
<223> OTHER INFORMATION: Primer 4 (reverse primer)

<400> SEQUENCE: 8

```
taaaatggcg aatccaattc caagagg                                        27
```

<210> SEQ ID NO 9
<211> LENGTH: 63
<212> TYPE: DNA
<213> ORGANISM: Artificial Sequence
<220> FEATURE:
<223> OTHER INFORMATION: Resulting DNA Fragment

<400> SEQUENCE: 9

```
aagcattccc gggcgggtgg atgacccagc ayggtccctc ttggaattgg attcgccatt    60
tta                                                                  63
```

<210> SEQ ID NO 10
<211> LENGTH: 63
<212> TYPE: DNA
<213> ORGANISM: Artificial Sequence
<220> FEATURE:
<223> OTHER INFORMATION: Resulting DNA Fragment

<400> SEQUENCE: 10

```
taaaatggcg aatccaattc caagagggac crtgctgggt catccacccg cccgggaatg    60
ctt                                                                  63
```

<210> SEQ ID NO 11
<211> LENGTH: 79
<212> TYPE: DNA
<213> ORGANISM: Artificial Sequence
```

```
<220> FEATURE:
<223> OTHER INFORMATION: FMS-related tyrosine kinase1 DNA Fragment

<400> SEQUENCE: 11
ttttgggctg cagggctggc ccagtggggt acatgatgca ttgggtgatc agtgcagctc    60
ctcaatcaaa ctggtcctg                                                 79

<210> SEQ ID NO 12
<211> LENGTH: 31
<212> TYPE: DNA
<213> ORGANISM: Artificial Sequence
<220> FEATURE:
<223> OTHER INFORMATION: Primer 5 (forward primer)

<400> SEQUENCE: 12
ggctgcaggg ctggcccagg atgtggggta c                                   31

<210> SEQ ID NO 13
<211> LENGTH: 30
<212> TYPE: DNA
<213> ORGANISM: Artificial Sequence
<220> FEATURE:
<223> OTHER INFORMATION: Primer 6 (reverse primer)

<400> SEQUENCE: 13
ccagtttgat tgaggagctg cactgatcac                                     30

<210> SEQ ID NO 14
<211> LENGTH: 73
<212> TYPE: DNA
<213> ORGANISM: Artificial Sequence
<220> FEATURE:
<223> OTHER INFORMATION: Resulting DNA Fragment

<400> SEQUENCE: 14
ggctgcaggg ctggcccagg atgtggggta crtgatgcat tgggtgatca gtgcagctcc    60
tcaatcaaac tgg                                                       73

<210> SEQ ID NO 15
<211> LENGTH: 73
<212> TYPE: DNA
<213> ORGANISM: Artificial Sequence
<220> FEATURE:
<223> OTHER INFORMATION: Resulting DNA Fragment

<400> SEQUENCE: 15
ccagtttgat tgaggagctg cactgatcac ccaatgcatc aygtacccca catcctgggc    60
cagccctgca gcc                                                       73

<210> SEQ ID NO 16
<211> LENGTH: 511
<212> TYPE: DNA
<213> ORGANISM: Homo sapiens

<400> SEQUENCE: 16
tgacaagccg aggcggtgag ccgggcagga ggaaggagcc tccctcaggg tttcgggaac    60
cagatctctc accaggaaag actgatacag aacgatcgat acagaaacca cgctgccgcc   120
accacaccat caccatcgac agaacagtcc ttaatccaga aacctgaaat gaaggaagag   180
gagactctgc gcagagcact ttgggtccgg agggcgagac tccggcggaa gcattcccgg   240
gcgggtgacc cagcayggtc cctcttggaa ttggattcgc catttttattt ttcttgctgc   300
```

-continued

```
taaatcaccg agcccggaag attagagagt tttatttctg ggattcctgt agacacaccc      360
acccacatac atacatttat atatatatat attatatata tataaaaata aatatctcta      420
ttttatatat ataaaatata tatattcttt ttttaaatta acagtgctaa tgttattggt      480
gtcttcactg gatgtatttg actgctgtgg a                                    511
```

<210> SEQ ID NO 17
<211> LENGTH: 511
<212> TYPE: DNA
<213> ORGANISM: Homo sapiens

<400> SEQUENCE: 17

```
agttgggagg ggaatgttcc cactcagatc ctgacaggga agaggaggag atgagagact       60
ctggcatgat cttttttttg tcccacttgg tggggccagg gtcctctccc ctgcccagga      120
atgtgcaagg ccagggcatg ggggcaaata tgacccagtt ttgggaacac cgacaaaccc      180
agccctggcg ctgagcctct ctaccccagg tcagacggac agaaagacag atcacaggta      240
cagggatgag gacacyggct ctgaccagga gtttggggag cttcaggaca ttgctgtgct      300
ttggggattc cctccacatg ctgcacgcgc atctcgcccc caggggcact gcctggaaga      360
ttcaggagcc tgggcggcct tcgcttactc tcacctgctt ctgagttgcc caggagacca      420
ctggcagatg tcccggcgaa gagaagagac acattgttgg aagaagcagc ccatgacagc      480
tccccttcct gggactcgcc ctcatcctct t                                    511
```

<210> SEQ ID NO 18
<211> LENGTH: 300
<212> TYPE: DNA
<213> ORGANISM: Homo sapiens

<400> SEQUENCE: 18

```
tcttttctcc cttgcttttt gcttttttc cttttcctcc tcacatgtct taggcctgct       60
agaggactcc cgagatgttg ctcaggccag ccagtgatcc ctggggctaa cgggcttgtt      120
gccctgggtt ttgggctgca gggctggccc agtgggtac rtgatgcatt gggtgatcag      180
tgcagctcct caatcaaact ggtcctgcgt gccctgaggt ggcgggggtt ggagcaggga      240
agtcattggg tttaggaagg atttctctaa cactgagtaa catgaggatt tagcagtagt      300
```